United States Patent
Schwarz-Hartmann et al.

[11] Patent Number: 5,974,615
[45] Date of Patent: Nov. 2, 1999

[54] ROTARY ELECTRIC TOOTHBRUSH WITH STROKE-TYPE BRISTLE MOVEMENT

[75] Inventors: Armin Schwarz-Hartmann, Albig; Karl Herzog, Frankfurt; Peter Hilfinger, Bad Homburg, all of Germany

[73] Assignee: Braun Aktiengesellschaft, Frankfurt, Germany

[21] Appl. No.: 08/739,092

[22] Filed: Oct. 28, 1996

[30] Foreign Application Priority Data

Jul. 10, 1996 [DE] Germany .................. 196 27 752

[51] Int. Cl.⁶ .................................................. A46B 13/02
[52] U.S. Cl. .................. 15/22.4; 15/28; 15/22.1; 74/23
[58] Field of Search .................. 15/28, 29, 22.1, 15/23, 167.1, 24, 22.2, 22.4; 74/23; 601/101, 109, 114, 95

[56] References Cited

U.S. PATENT DOCUMENTS

| | | | |
|---|---|---|---|
| 1,212,440 | 1/1917 | Becker | 74/570 |
| 1,795,098 | 3/1931 | Scadding | 15/23 |
| 1,869,991 | 8/1932 | White et al. | 15/22.4 |
| 2,379,049 | 6/1945 | Tompkins | 15/22.1 |
| 2,549,551 | 4/1951 | Baker | 74/42 |
| 2,618,161 | 11/1952 | Manson | 15/23 |
| 2,844,965 | 7/1958 | Stelljes et al. | 74/70 |
| 2,858,701 | 11/1958 | Willcox | 15/23 |
| 3,046,584 | 7/1962 | Wepfer | 15/22 |
| 3,106,732 | 10/1963 | Dayton et al. | 15/28 |
| 3,447,177 | 6/1969 | Williams et al. | 15/23 |
| 3,675,330 | 7/1972 | Drapen et al. | 15/28 |
| 3,699,952 | 10/1972 | Waters et al. | 128/24.2 |
| 3,864,779 | 2/1975 | Thomas | 15/22 |
| 3,939,599 | 2/1976 | Henry et al. | 15/28 |
| 3,978,852 | 9/1976 | Annoni | 128/62 A |
| 4,253,212 | 3/1981 | Fujita | 15/167 R |
| 4,326,314 | 4/1982 | Moret et al. | 15/22 |
| 4,450,599 | 5/1984 | Scheller et al. | 15/22 R |
| 4,476,604 | 10/1984 | White et al. | 15/105 |
| 4,603,448 | 8/1986 | Middleton et al. | 15/22 |
| 4,698,869 | 10/1987 | Mierau et al. | 15/22 R |
| 4,756,202 | 7/1988 | Kawamoto | 74/23 |
| 4,974,278 | 12/1990 | Hommann | 15/22 |
| 5,054,149 | 10/1991 | Si-Hoe et al. | 15/28 |
| 5,088,145 | 2/1992 | Whitefield | 15/22.1 |
| 5,145,369 | 9/1992 | Lustig et al. | 433/118 |
| 5,311,633 | 5/1994 | Herzog et al. | 15/28 |
| 5,493,747 | 2/1996 | Inakagata et al. | 15/22.1 |
| 5,577,285 | 11/1996 | Drossler | 15/22.1 |

FOREIGN PATENT DOCUMENTS

| | | |
|---|---|---|
| 0 110 327 | 11/1983 | European Pat. Off. . |
| 0 054 043 | 6/1985 | European Pat. Off. . |
| 327 876 | 8/1989 | European Pat. Off. . |
| 2 368 854 | 10/1976 | France . |
| 2 002 351 | 1/1970 | Germany . |
| 4002199 | 7/1991 | Germany ............. 15/22.1 |
| 3-173558 | 7/1991 | Japan . |
| 384 539 | 7/1961 | Switzerland . |
| 609 238 | 2/1979 | Switzerland . |
| 369600 | 3/1932 | United Kingdom . |
| WO 91/07116 | 5/1991 | WIPO . |
| WO 93/10721 | 6/1993 | WIPO . |
| WO 94/12121 | 6/1994 | WIPO . |
| WO 94/23667 | 10/1994 | WIPO . |

*Primary Examiner*—Gary K. Graham
*Attorney, Agent, or Firm*—Edward S. Podszus; Chester Cekala

[57] ABSTRACT

An electric toothbrush (1) is described which incorporates a handle (2) and a brush attachment (3). The handle (2) houses an electric motor (8). Protruding from the handle (2) is a shaft (20), which is coupled to the electric motor (8). The brush attachment (3) can be mounted on the handle (2). The brush attachment (3) supports a bristle head (26) which can be coupled to the shaft (20), and from which protrude a multiplicity of bristles (4). In the operating mode, the bristle head (26) describes a rotary motion (49) and a stroke motion (50), with the frequency of the stroke movement (50) being higher, and preferably substantially higher, than the frequency of the rotary movement (49.) The stroke movement (50) provides a poking action of the bristles (4), which serves to loosen plaque from dental surfaces. The rotary movement (49) serves to wipe away plaque loosened from the dental surfaces.

72 Claims, 4 Drawing Sheets

ROTARY ELECTRIC TOOTHBRUSH WITH STROKE-TYPE BRISTLE MOVEMENT

This invention covers an electric toothbrush with a handle which houses an electric motor, and from which projects a shaft that is connected to and driven by said electric motor, and can be coupled to a brush attachment. Said electric motor, when switched on, causes said shaft to oscillate or to rotate in continuous fashion around the longitudinal axis of said shaft.

An electric toothbrush of this type has been described in international patent application WO 94/12121 A1. In that particular design, the brush attachment incorporates a rotating brush shaft which can be driven in alternating fashion. The bristle head pivots on the brush attachment, with the axis of rotation of the brush shaft and the axis of rotation of the bristle head extending in an essentially perpendicular relation to each other. The design example shown in FIG. 9 of international patent application WO 94/12121 A1 features a T-adapter that consists of a longitudinal rod and a cross pin. The longitudinal rod is seated in a bore in the brush shaft roughly parallel with, but outside its axis of rotation. The cross pin is seated in a bore in the bristle head roughly parallel with but outside its axis of rotation. The longitudinal rod can be turned in its bore and can be shifted in the direction of the axis of rotation of the brush shaft. The cross pin, on its part, can rotate in its bore but cannot move in its bore in the direction of the axis of rotation of the bristle head. Alternating the direction of rotation of the brush shaft around its axis of rotation causes the bristle head to follow with an alternating rotary movement around its axis of rotation, but because the cross pin cannot shift its position in its bore, the bristle head moves in an alternating stroke fashion. This stroke movement takes place in a direction parallel with the axis of rotation of the bristle head. The frequency of the alternating rotary movement of the bristle head is identical to the frequency of the back-and-forth stroke movement of the bristle head.

The back-and-forth stroke movement of the bristle head causes the bristles to act like pokes and picks which makes it possible to loosen plaque from the dental surfaces of the user. The alternating rotary movement of the bristle head causes the bristles to work like wipers which can remove especially plaque that has been loosened from the dental surfaces by the poking movement. The combination of these movements provides for good cleaning of the user's teeth.

This earlier design, however, is relatively complex; also, it is not helped by the fact that the mechanical components which produce the stroke movement are located directly underneath the bristle head. During brushing, this part of the brush attachment is penetrated by toothpaste, saliva or water, and it is especially the toothpaste with its abrasive particles that leads to a relatively quick wear of the mechanical moving parts. Moreover, only the bristle head itself, and not the entire brush attachment makes the additional back-and-forth stroke movement which some users consider to be unpleasant. Finally, the particular structural configuration of this earlier electric toothbrush design involves a rigid coupling of the frequency of the bristle head's back-and-forth stroke movement to the frequency of the oscillating rotary movement of the bristle head. That does not make it possible, for example, to further increase the stroke frequency of the bristle head by simple mechanical means so as to obtain more effective poking of the bristles on the dental surfaces, while maintaining a constant frequency of the oscillating rotary movement. This rigid, phase-locked coupling of the two movements of the bristle head causes the bristle head to vibrate in a certain way which users find bothersome, and which makes it more difficult to accurately position the free bristle ends on the dental surface.

The objective of the invention here described is to provide an electric toothbrush of the type mentioned above, which further improves dental cleaning.

According to the invention, this objective is essentially met by a design whereby the shaft is subjected to an oscillating swivel, lift-stroke or similar movement in a direction which is essentially perpendicular to its axis.

By virtue of this approach, it is no longer necessary to position components which serve to produce the swivel or stroke movement in the brush attachment itself, since the entire shaft is subjected to a swivel, lift or similar motion component inside the handle, which generates the stroke movement of the bristle head. The handle is typically sealed off against toothpaste, moisture and the like, which prevents premature wear of the mechanical parts located inside the handle. Also, the entire brush attachment that is snapped onto the shaft is set in swivel or lift-stroke motion, which the majority of users find more pleasant. Finally, it is possible to freely select the frequency of the swivel, stroke or other movement of the shaft, eliminating the rigid coupling of the lift or swivel frequency to that of the oscillating rotary movement of the bristle head.

In a particularly desirable configuration according to this invention, the swivel, lift-stroke or other movement of the shaft takes place around an axis which extends in an essentially perpendicular direction relative to the longitudinal axis of the shaft. In particular, the shaft can be mounted in the handle in such a way as to swivel axially, for instance, in rocker-like fashion. In the context of this description, the term swivel is to be understood as a movement of the shaft over its entire length while the term lift or stroke refers to the movement of an end section of the shaft, or of the bristle head that is mounted on the shaft. For instance, while the shaft in its entirety swivels rocker-like, the movement of the end points of the rocker, especially in the case of an elongated lever arm, can be viewed as a type of stroke or lift movement. For improved dental cleaning it is ultimately of importance that the bristles follow a sort of poking movement, meaning a movement in the direction of the longitudinal axis of the bristles: i.e., the longitudinal axis or rotary axis of the bristle head, which is essentially brought about by the stroke movement of the free end of the shaft.

In another design variation according to this invention, it has been found to be advantageous to provide the brush attachment with a bristle head supporting a multiplicity of bristles: said bristle head, as part of the brush attachment that is coupled to the shaft, makes both a rotary and a swivel or lift-stroke movement. This is a practical way for the lift-stroke of the bristle head to impart to the bristles a certain poking motion which serves to loosen plaque from the surfaces of the user's teeth. The rotary movement of the bristle head essentially provides a wiping effect of the bristles on dental surfaces, helping to remove plaque from the dental surfaces.

It has also desirable to set the frequency of the swivel or stroke movement at a higher level than the frequency of the rotary movement, and preferably at two to three times the rate of the latter.

The direction of the rotary movement and the direction of the swivel or stroke movement preferably extend at a right angle to each other.

The amplitude of the swivel or lift-stroke movement, especially of the bristle head (i.e. the bristle tips), is in the range between about ±0.02 mm and about ±0.2 mm, and preferably about ±0.05 mm.

In a preferred design example, the frequency of the rotary movement is set at about 60 to 70, and ideally about 65 Hz, while the frequency of the swivel or stroke movement is set at about 120 to 210 Hz, and preferably about 165 Hz.

The specific frequencies for the rotary movement and the swivel or stroke movement in relation to each other are so chosen that phase coincidence of the heterodyne oscillations does not occur until after several oscillatory cycles, and specifically after more than four such cycles. Given different frequencies of the two motions of the bristle head, the curve of the resulting movements takes on a very irregular slope. This irregular curve repeats itself after a certain number of cycles of the two individual movements. According to prior art, the stroke movement has a frequency twice as high as the oscillating rotary movement, so that the irregular curve repeats itself with the periodicity of the oscillation cycles. Such frequent occurrence of the irregular motion curve and the associated unsteadiness in the movement of the bristle head do not always make it easy for the user to positively and firmly press the free bristle ends against the teeth, or to accurately position the bristles on the dental surfaces. If, however, the frequency relation of the rotary-movement and the swivel- or stroke-movement frequencies is selected in a way that, after canceling out identical errors, the quotient displays large incommensurable numbers or prime-number products, the curve irregularities of the overall movement of the bristle head occur quite seldom. The less often these irregularities are encountered, the smoother the motion of the bristle head and the easier the exact positioning of the free bristle ends on the user's teeth. Individual prime-number quotients for said frequency relation may, for instance, be 23/9, 13/5, 27/10, 28/11, 34/13, 171/65. Given these conditions, the quotient from the two frequencies, and thus the mutual relation of the two frequencies is changed in a minor way only, while phase coincidence occurs after a varying, large number of oscillations or oscillatory cycles, these being 9.5, 10, 11, 13, 65. The greater the number of oscillation cycles, the smoother and more regular the resulting motion of the bristle head.

All in all, it has been found that such frequency differential of the lift-stroke and the rotary movement significantly improves the cleaning effect on a user's teeth. This is attributable to the fact that, on the one hand, the higher frequency of the stroke movement of the bristle head intensifies the poking and picking movement of the bristles, thus producing significantly enhanced loosening of plaque from the user's dental surfaces. On the other hand, the wiping motion does not take place at the same high frequency and too rapid a wiping of the bristles over the dental surfaces is thus avoided. Instead, the wiping motion takes place at a lower frequency, which permits positive removal of the loosened plaque from the dental surfaces and, in fact, helps loosen additional plaque. In other words, while the higher frequency of the lift-stroke movement of the bristle head is better for loosening plaque from a user's teeth, the lower frequency of the rotary movement of the bristle head assures positive removal of the loosened plaque and helps loosen more plaque.

In a desirable, enhanced design version according to this invention, the mutual relation of the frequencies of the rotary movement and the lift-stroke movement is a finite value, or a periodic fraction, or a non-periodic fraction. It is thus possible to freely select the frequency relation between the rotary movement and the stroke movement within this range. For example, given a fixed, pre-established frequency for the rotary movement, it is a simple matter to set the higher frequency for the stroke movement at the desired rate by selecting the appropriate frequency ratio.

In another desirable, enhanced design version according to this invention, the frequencies of the rotary movement and the stroke movement are independent of one another. By suitable structural means, the frequency of the rotary movement and the frequency of the stroke movement can be freely set at the respectively desired value, absolutely independent of each other.

In a practical embodiment of this invention, the rotary movement and the lift-stroke movement of the bristle head are generated by the electric motor. Only one motor is used. The different frequencies for the rotary movement and, respectively, the stroke movement can be produced by this electric motor with the aid of a gear system or similar device. In that case, the ratio between the frequency of the rotary movement and that of the stroke movement is determined by the gear ratio. It is also possible, however, to generate these frequencies without a gear system. This can be accomplished by means of a coupling or similar device which may be interpositioned between the stroke movement and the lower-frequency rotary movement.

In another practical design version according to this invention, the rotary movement is generated by the electric motor, while the stroke movement is independently generated by other drive provisions. In other words, the rotary movement and the stroke movement are each operated by mutually independent drive systems. This makes it easily possible to independently set the frequency of the rotary movement and the frequency of the stroke movement at any desired value. By the same token, the ratio of the rotary-movement and stroke-movement frequencies can also be set at any desired value.

In this context, it is desirable to drive the stroke movement with a second electric motor, or an electromagnetic oscillator, or a piezoelectric actuator. While the rotary movement is generated by the primary electric motor, the stroke movement is produced by a second drive system, preferably a second electric motor. In that case, appropriate controls for the two electric motors permit mutually independent selection of the frequency for the rotary movement and the frequency for the stroke movement.

In an enhanced design version of this invention, the lift-stroke movement of the bristle head can be switched off when a certain force level bearing on the bristles is exceeded.

As explained above, the stroke movement of the bristle head produces a poking effect of the bristles which serves to loosen plaque from the dental surfaces. According to this invention, the higher frequency of the stroke movement intensifies that poking effect. It is a known fact that many users of electric toothbrushes often have a tendency to press the bristle ends against their teeth with too much force. While this further strengthens the poking action of the bristles, it is also a known fact that excessive force applied to the dental surfaces or to the gums can cause damage. To avoid such damage, the stroke movement switches itself off as soon as the force applied to the bristles exceeds a predetermined level, thus safely avoiding possible damage. Also, the interruption of the stroke movement alerts the user in tactile and/or acoustic fashion to the fact that he is pushing the bristles against his teeth with too much pressure. This is signaled by the poking movement of the bristles, which the user feels in the form of vibrations on his dental surfaces, the stoppage of which tells him that the poking action has been turned off. This shut-off feature of the stroke movement thus provides a particularly useful safety and alert function for the user.

In another desirable design version according to this invention, the lift-stroke movement can be switched off by the user. In other words, the user is free at any time to activate or deactivate the stroke movement of the bristle head, and thus the poking action of the bristles on his dental surfaces. This may be useful, for instance, when the user merely wants to massage his gums, in which case the poking action would be unpleasant. This allows the user to temporarily switch off the poking action.

In a practical design version according to this invention, the rotary movement is an alternating motion around an axis that is approximately parallel with the bristles of the bristle head. It has been found that this produces a particularly good wiping effect of the bristles which permits especially effective removal of the loosened plaque, and which also helps loosen additional plaque from the dental surfaces.

In another practical design version according to this invention, the stroke movement of the bristle head is approximately parallel with the bristles. When the user places the bristles on his dental surfaces in roughly perpendicular fashion, this will cause the poking action of the bristles to be applied on the teeth in equally perpendicular fashion, which makes this poking action of the bristles particularly good and effective. It further enhances the loosening of plaque, and thus the cleaning of the dental surfaces.

In another practical design version according to this invention, the shaft and the brush attachment are integral parts of a rocker arm which is swivel-mounted inside the handle at an angle roughly perpendicular to the shaft. When the rocker arm swivels, the bristle head mounted at the free end of the brush attachment makes a reciprocating stroke motion. The perpendicular arrangement of the pivot spindle of the rocker arm relative to the shaft causes the stroke movement of the bristle head to be in the approximate direction of the bristles. Likewise, suitable selection of the distance between the bristle head and the rocker-arm spindle can cause the stroke movement of the bristle head to be approximately parallel with the direction in which the bristles extend. This produces the aforementioned, effective poking action of the bristles, and thus results in better cleaning of the dental surfaces. Configuring the shaft and the brush attachment as parts of a rocker arm thus offers the possibility of obtaining the desired stroke motion of the bristle head in a simple and cost-effective manner.

In a practical, enhanced design version according to this invention, the electric motor is coupled to means for generating vibrations, which acts on a cantilever that protrudes from the rocker arm opposite the brush attachment. The rocker arm is thus vibrated, i.e., set in a very rapid swivel motion of the rocker arm around its spindle. As a result, the bristle head at the free end of the brush attachment follows a very rapid reciprocating stroke motion. When the user applies the bristles of the bristle head to his dental surfaces, this stroke motion of the bristle head results in the aforementioned poking action of the bristles which loosens plaque from the dental surfaces. The rocker arm and the above-mentioned vibration effect thus produce the poking action of the bristles in a simple and practical fashion.

In a desirable embodiment of this invention, said vibration is generated by means of an eccentric cam mounted on the motor shaft of the electric motor, and bearing on the cantilever of the rocker arm. The cam on the motor shaft generates the vibration, and since the cam bears on the cantilever, the vibration is transferred to the rocker arm. This provides an extremely simple approach to setting the rocker arm in vibratory motion, thus producing the poking action of the bristles. It requires very few additional components, which are inexpensive to make. On its part, the configuration of the cam offers an easy way to select the mode and strength of the vibration.

In an enhanced embodiment of this invention, the cantilever is provided with a guide shoe, or roller, on which bears the above-mentioned eccentric cam. Any friction of the cam on the cantilever is thus reduced, or altogether eliminated. The vibration is thus generated without wear, which is especially useful given daily operation.

In a further enhancement of the design according to this invention, the eccentric element is provided in the form of a bearing, in particular, a ball bearing having an eccentric inner race, mounted on the motor shaft. The cantilever of the rocker arm bears on the outer ring of the ball bearing. The use of this ball bearing prevents any friction losses between the motor shaft and the cantilever. Vibration is generated without any wear. The degree of eccentricity of the inner bearing race permits simple selection of the mode and strength of the vibration. This is a particularly strong and sturdy means for vibrating the rocker arm, and generating the poking action of the bristles.

It is also possible to provide the cantilever with a roller which bears on the outer ring of the ball bearing. This will further reduce any friction. In this case, the outer ring of the ball bearing can itself be eccentric. This produces the superposition of two eccentric motions: that of the inner race and that of the outer ring of the ball bearing, permitting additional modulation of the vibration of the rocker arm and thus of the poking action of the bristles.

In a desirable embodiment of this invention, the vibration-generating element is an eccentric roller which is attached to the cantilever and bears on the motor shaft. In other words, the eccentric element in this configuration is a part of the cantilever, and the motor shaft does not support any such component. The eccentric roller only bears on the motor shaft; in this fashion, the vibration of the rocker arm, and with it the poking action of the bristles, is generated. This configuration requires but few additional components, permitting simple and cost-effective production. The friction between the motor shaft and the eccentric roller is minor so that this configuration largely avoids any wear and lends itself to everyday use.

In a practical embodiment of this invention, a spring, in particular a spiral spring, is provided for pressing the cantilever against the eccentric element of the motor shaft, or the eccentric element of the cantilever against the motor shaft. The spiral spring thus ensures that the eccentric element always bears on the cantilever or, respectively, on the motor shaft, thus assuring vibration at all times. The selection of the spiral spring determines the amount of pressure with which the eccentric element bears on the cantilever or the motor shaft, respectively. This makes it possible to minimize the braking effect, and thus the load, of the vibration system on the electric motor. Instead of the spiral compression spring, a leaf-type flat spring, or a tension coil spring may be used as an alternative.

In a further enhancement according to this invention, the cantilever is lifted off the eccentric element on the motor shaft, or the eccentric element of the cantilever is lifted off the motor shaft, as the case may be, whenever the force applied to the bristles of the bristle head exceeds a certain level. Suitable selection of the spring tension permits selection of the pressure with which the cantilever is pushed against the eccentric element on the motor shaft, or the eccentric element on the cantilever against the motor shaft. When that pressure level is exceeded, the cantilever will be lifted off the eccentric element, or the eccentric element off the motor shaft. As a result, the rocker arm no longer vibrates and the bristle head stops its reciprocating movement. As stated above, this constitutes a safety and signaling function for the user in terms of excessive pressure exerted by the bristles on his dental surfaces. The spring thus provides the above-mentioned safety and signaling function in a very simple, low-cost, yet safe and effective way.

In an enhanced embodiment of this invention, the rocker arm is provided with a tube facing the brush attachment, which holds the shaft and resiliently protrudes from the handle section. The tube with the shaft in it constitute a free end of the rocker arm, which extends from the handle. The part of the tube that protrudes from the handle can accommodate the brush attachment. As explained above, when the motor is switched on the rocker arm is set in vibratory motion which, in turn, produces the reciprocating stroke movement of the bristle head. To prevent the protrusion of the tube from the handle from interfering with this reciprocating movement, the tube is connected with the handle in an elastic fashion. This permits unimpeded propagation of the rocker arm vibration, and equally unimpeded backand-forth stroke movement of the bristle head. The elastic extension of the tube from the handle thus provides for proper functioning of the stroke movement in a simple, yet effective manner. As an added benefit, the elastic connection securely prevents dirt and especially water from penetrating into the inside of the electric toothbrush.

In another desirable embodiment of this invention, the motor shaft of the electric motor, and the spindle which is part of the rocker arm assembly are connected with each other by a quadrilateral link. The motor shaft of the electric motor turns in a continuous rotational mode. By means of the quadrilateral link, this continuous rotation of the motor shaft is converted into an alternating rotary movement of the rocker arm spindle. As a result, the bristle head which is coupled to this spindle rotates in alternating fashion. This quadrilateral link offers a well-established, simple, low-cost approach to the rotary conversion mentioned. The quadrilateral link also has the advantage that the vibration of the spindle does not affect the alternating rotation of the spindle. In essence, the quadrilateral link compensates for the swivel movement of the spindle in such a way as to essentially cancel it out, so that it does not negatively affect the motor shaft of the electric motor. This compensation for the swivel movement of the spindle is accomplished by the connecting joints of the individual components of the quadrilateral link, i.e., especially by virtue of the 'play' or slack in relation to one another. The alternating rotary movement is thus generated by the quadrilateral link, independent of the generation of the vibratory movement.

In another enhanced embodiment of this invention, a frame is provided which holds the rocker arm, and which is housed inside the handle. This prevents direct transmission of the vibrations generated by the rocker arm to the handle. This makes the use of the electric toothbrush more pleasant, and thus constitutes an advantageous feature in terms of user comfort. This also makes it possible during production of the electric toothbrush to test the rocker arm, in simple fashion and outside the handle, for proper functioning, and thus for its vibrating action. Similarly, repairs and corrections are easily made on the frame and the components it supports while outside the handle. This is a substantial benefit in terms of the cost of manufacture and maintenance of the electric toothbrush.

In a desirable enhancement of the design according to this invention, said frame also holds the electric motor. As mentioned above, this substantially facilitates the manufacture, testing and maintenance of the electric toothbrush, and thus has a positive effect on the cost of the product.

In a further design enhancement, said frame is elastically mounted in the handle: i.e., the frame is elastically supported inside the handle. As a result, the vibrations generated by the rocker arm are not transferred to the handle, which makes operation more pleasant and further adds to user comfort.

Additional features, advantages and applicational possibilities of this invention are reflected in the following description of design examples, which are explained in more detail with the aid of the attached diagrams. In this context, all features described or depicted, whether individually or in any reasonable combination, constitute the object of this invention irrespective of their associative configuration in the claims or the cross references of the latter.

In the diagrams:

FIGS. 1 to 3 show a first design example of an electric toothbrush (1), serving to clean a user's teeth, and to remove plaque from dental surfaces.

Figure 1:
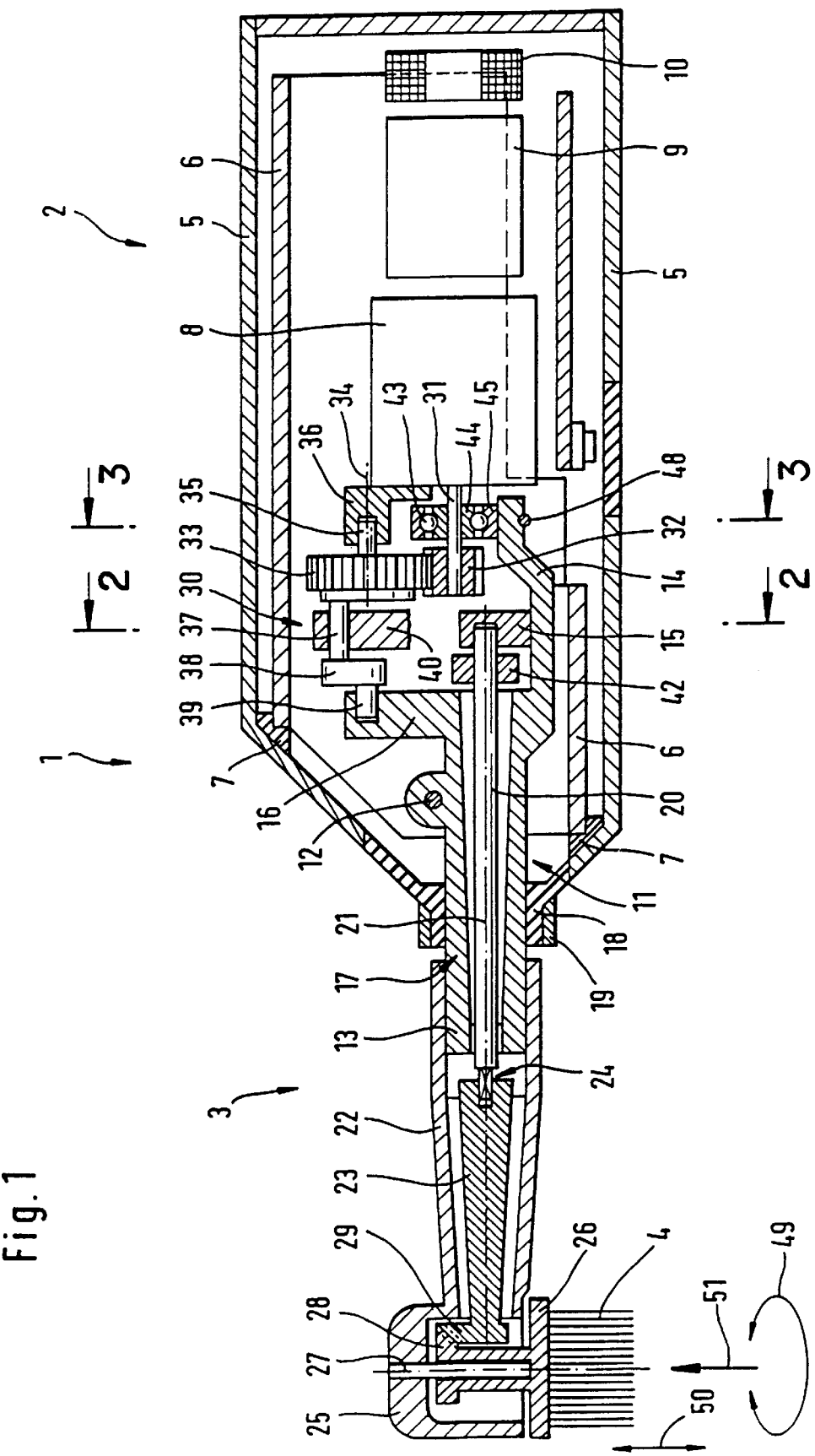
FIG. 1 is a schematic illustration, along a longitudinal section, of a first design example of an electric toothbrush.

The electric toothbrush includes a roughly cylindrical, elongated handle (2). A brush attachment (3), itself in roughly cylindrical, elongated form, can be mounted on the handle (2). The diameter of the handle (2) is so chosen that a user can hold the electric toothbrush by the handle (2) securely in his or her hand. The diameter of the brush attachment (3) is smaller than the diameter of the handle (2) to permit easy insertion of the brush attachment (3) in the user's mouth.

At the free end of the brush attachment (3), a multiplicity of bristles (4) protrude from the bristle head, serving to clean the user's teeth.

The handle (2) incorporates a housing (5), which accommodates a frame (6). The frame (6) is elongated and partly cylindrical, and extends over almost the entire length of the housing (5), and thus of the handle (2). At its end facing the brush attachment (3), the frame (6) is elastically held in place in the housing (5) by means of cushions (7), consisting of plastic or rubber or a similar material.

Attached to the frame (6) are an electric motor (8), a battery (9) and additional electronic components such as a charging coil (10) and the like. These components are arranged one behind the other in the longitudinal direction of the handle (2). Also attached to the frame (6) is a rocker arm (11), which can swivel around the spindle (12). The rocker arm (11) with the spindle (12) is located in the section of the handle (2) that faces the brush attachment (3). Part of the rocker arm (11) protrudes from the handle (2).

The rocker arm (11) incorporates a tube (13), a cantilever (14), and two support stems (15), (16). The tube (13) of the rocker arm (11) extends through an opening (17) in the end of the handle (2), facing the brush attachment (3), and protrudes from the handle (2). Located between the tube (13) and the housing (5) of the handle (2) is an annular diaphragm (18), made of plastic, rubber or a similar material, by way of which the tube (13) of the rocker arm (11) extends elastically from the handle (2). Holding and retaining the tube (13) in the housing (5) of the handle (2) is a clamp (19), which surrounds the diaphragm in ring-shaped fashion.

At least that part of the tube (13) that extends from the handle (2) has a cross section that is contoured on the outside. It is on this protruding part of the tube (13) that the brush attachment (3) can be mounted. At its end that faces the handle (2), the brush attachment has a cross section that is contoured on the inside in such a way as to match the outer contour of the tube (13). The matching contours are formed in such a way that the brush attachment (3) can be mounted on the handle (2) in only one particular angular position. For example, the contour may have a star-shaped, or triangular, or similar configuration.

When mounted on the tube (13) of the rocker arm (11), the brush attachment (3) becomes an integral part of the rocker arm (11).

Located in the tube (13) of the rocker arm (11) is a spindle (20), which is pivot-mounted at one end, on the free end of the tube (13), protruding from the handle (2) and, at the other end, on the support stem (15). The spindle (20) extends roughly in the longitudinal direction of the handle (2) and the brush attachment (3), and defines an axis (21). The spindle (20) constitutes another component of the rocker arm assembly (11). This spindle (20) protrudes from the tube (13) where, at its free end, it is contoured on the outside.

The axis (12) of the rocker arm (11), and the axis (21) of the spindle (20) extend roughly perpendicular to each other.

The tube (13) of the rocker arm (11) accepts the brush attachment (3). The brush attachment (3) is provided with a support tube (22), in which a brush shaft (23) is pivot-mounted. When the brush attachment (3) is mounted, the brush shaft (23) is concentric with the axis (21); at its end facing the handle (2), it has a recess (24). This recess (24) has a cross section with an inside contour which corresponds to the outer contour of the shaft (20) that protrudes from the tube (13). The matching contours are configured in a way that the shaft (20) can be inserted in the recess (24) in several angular positions. For example, the contour may be square.

The free end of the support tube (22), and thus the free end of the brush attachment (3), holds a receptacle (25) which houses a bristle head (26) with the bristles (4). The bristle head (26) is disk-shaped, and can swivel around a pin (27). The pin (27) extends through the center of the disk of the bristle head (26); the bristles (4) extend away from the bristle head (26), approximately parallel with the pin (27).

The pin (27) of the bristle head (26) extends roughly perpendicular to the axis (21) of the spindle (20), and also approximately perpendicular to the axis (12) of the rocker arm.

By way of two bevel gear segments (28, 29), an alternating rotary movement of the brush shaft (23) around the axis (21) can be translated into an alternating rotary movement of the bristle head (26) around the pin (27).

It should be noted that said translation of the alternating rotary movement from the brush shaft (23) to the bristle head (26) can be accomplished in other ways as well. It is possible, for example, to perform this translation in accordance with the aforementioned prior art described in the international patent application WO 94/12121 A1, particularly as shown in FIGS. 1 and 7 of that document. To that extent, express reference is made in this application to the information disclosed in WO 94/12121 A1.

Between the rocker arm (11) and the electric motor (8), the handle houses a quadrilateral link (30). In adaptation thereto, the electric motor (8) has a motor shaft (31), which extends approximately parallel with the axis (21) of the spindle (20), and protrudes from the electric motor (8) in the direction of the rocker arm (11). Rotationally fixed on the motor shaft (31) is a pinion (32), which meshes with a spur gear (33). The spur gear (33) is pivot-mounted on a shaft (34), which extends approximately parallel with the motor shaft (31). A lug (35), positioned in a support stem (36) that is held by the electric motor (8), extends from the spur gear (33) concentric with the shaft (34).

On the side of the spur gear (33) opposite the lug (35), a drive crank (37) is attached to the spur gear (33), extending essentially parallel with, but at a distance from the shaft (34). This crank (37) is also pivot-mounted in the support stem (16) of the rocker arm (11), by way of a connector (38) and a tenon (39). The tenon 39 is concentric with the shaft (34).

A connecting rod (40) is attached in a rotating form to the crank (37). As can be seen especially in FIG. 2, the connecting rod (40) is swivel-connected to a crank (42) by means of a pin (41). Between the tube (13) and the support stem (15), the crank (42) is fixed to the spindle (20) of the rocker arm (11).

A ball bearing (43) is mounted on the motor shaft (31) of the electric motor (8). The ball bearing (43) has an eccentric inner race (44), and a concentric outer race (45). It is with the eccentric inner race (44) that the ball bearing (43) is seated on the motor shaft (31). The eccentric inner race (44) thus acts as the imbalance. The concentric outer race (45) is in contact with the free end of the cantilever (14) of the rocker arm (11).

Figure 3:
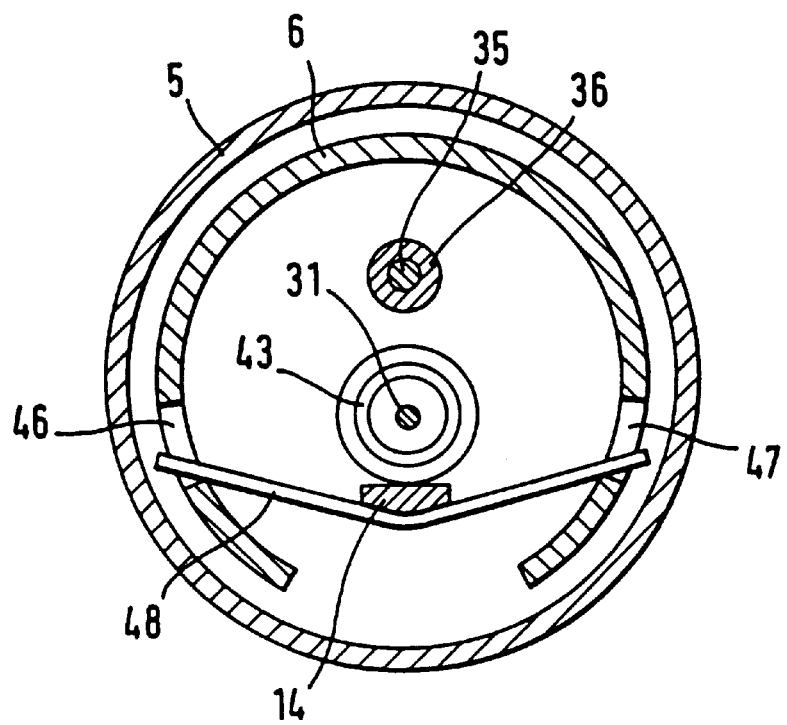
FIG. 3 is a schematic illustration of the electric toothbrush per FIG. 1, showing a cross section along the plane 3—3 in FIG. 1.

As can be seen especially in FIG. 3, the frame (6) is provided with openings (46, 47), which hold a leaf spring (48) in place by its free ends. The leaf spring (48) is positioned in a way that it bears on the cantilever (14) of the rocker arm (11), pressing it against the outer race (45) of the ball bearing (43). The pressure with which the leaf spring (48) pushes the cantilever (14) against the ball bearing (43) is a function of the elasticity constant of the leaf spring (48).

Figure 2:
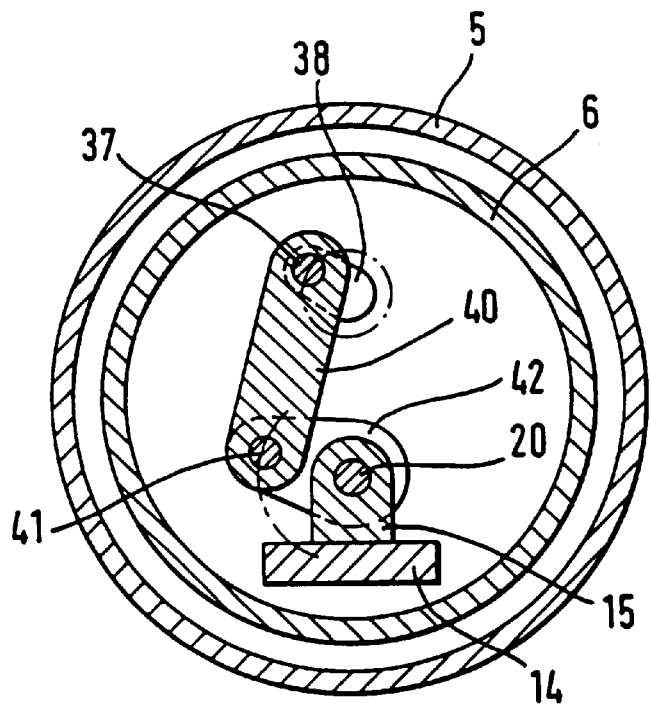
FIG. 2 is a schematic illustration of the electric toothbrush per FIG. 1, showing a cross section along the plane 2—2 in FIG. 1.

When the electric toothbrush (1) per FIGS. 1 to 3 is switched on, the motor shaft (31) of the electric motor (8) is set in rotating motion. By means of the quadrilateral link (30), this continuous rotation is translated into an alternating rotary movement of the shaft (20) around the axis (21). When the brush attachment (3) is mounted, this alternating rotary movement is transferred, by way of the bevel gear segments (28, 29), to the bristle head (26), which thus turns in an alternating rotary movement (49) around the pin (27). The bristle head (26) turns in an alternating rotary movement (49), within an angle of rotation the range of which may be between about ±15° and about ±40°. The overall travel can thus be between about 30° and about 80°. Preferably, the range of the angle of rotation is about ±30 degrees and the overall travel is thus about 60 degrees. However, angles of rotation of up to about ±90° are entirely feasible.

The frequency of the alternating rotary movement (49) of the bristle head (26) can be between about 50 Hz and about 80 Hz. Preferably, the frequency should be about 63 Hz.

As mentioned, when the electric toothbrush (1) per FIGS. 1 to 3 is in the operating mode, the motor shaft (31) of the electric motor (8) rotates in continuous fashion. Due to its eccentric inner race (44), the entire ball bearing (43) vibrates. In other words, the inner race (44) serves to generate the vibration. The cantilever (14), pressed against the outer race (45) of the ball bearing (43) by the leaf spring (48), transfers this vibration to the rocker arm (11). As a result, the rocker arm (11) is set into a vibrating swivel motion around the axis (12).

As explained above, the brush attachment (3), when mounted, constitutes an integral part of the rocker arm (11). Consequently, the brush attachment (3), along with the bristle head (26), is set into a vibrating swivel motion around the axis (12). Since the axis (12) is oriented approximately at a right angle to the pin (27), the bristle head (26) follows a reciprocating stroke movement (50), in a direction essentially parallel with the pin (27). This essentially parallel alignment of the bristles (4) and the pin (27) ultimately causes the bristles (4) to deliver a poking action in the direction in which the bristles extend.

The travel of the reciprocating stroke (50) of the bristle head (26), and thus the poking action of the bristles (4), can be over a distance in the range between about ±0.02 mm and about ±0.2 mm; the total travel thus being about 0.04 mm to about 0.4 mm. Preferably, this travel movement of the stroke (50) in either direction is about ±0.05 mm, and the overall travel is thus about 0.1 mm.

The frequency of the back-and-forth movement, i.e., reciprocating stroke (50) of the bristle head (26), and thus of the poking action of the bristles (4), can be between about 130 Hz and about 200 Hz, and is preferably about 164 Hz.

The frequency of the reciprocating stroke movement (50) is thus higher, and preferably substantially higher, than the frequency of the alternating rotary movement (49).

The rotary movement (49) and the stroke movement (50) of the bristle head (26) are both generated by the electric motor (8). The frequency of the reciprocating stroke (50) of the bristle head (26) corresponds directly to the rotational speed of the electric motor (8). The frequency of the alternating rotary movement (49) of the bristle head (26), however, is determined by the rotational speed of the electric motor (8) as modulated by the quadrilateral link (30). Accordingly, the frequency ratio of the alternating rotary movement (49) to that of the reciprocating stroke movement (50) is a finite value, or a periodic fraction, or a non-periodic fraction.

When the electric toothbrush (1), per FIGS. 1 to 3, is switched on for the purpose of cleaning the user's teeth, the user applies the bristles (4) to his dental surfaces. As a result, a certain force acts on the bristles (4), which is indicated in FIG. 1 by the numeral (51).

As has been explained, the cantilever (14) of the rocker arm (11) is pressed against the outer race (45) of the ball bearing (43) by means of a leaf spring (48). The cantilever (14) also pushes against that side of the ball bearing (43) on which the bristle head (26) is located. Now if the user applies a force (51) to the bristles (4) of the bristle head (26) which exceeds a certain level, the result will be that the cantilever (14) of the rocker arm (11) is lifted off the outer race (45) of the ball bearing (43), against the spring action of the leaf spring (48). The vibration generated by the ball bearing (43) is thus no longer transferred to the rocker arm (11) nor, consequently, to the bristle head (26) and the bristles (4). In other words, if and when the force 51 exceeds that certain level, the retraction of the cantilever (14) away from the ball bearing (43) will turn off the reciprocating stroke movement (50) of the bristle head, and with it the poking action of the bristles (4).

The specific pressure level of the force (51) at which the cantilever (14)is lifted off the ball bearing (43) can be predetermined by the selection of the appropriate elasticity constant of the leaf spring (48). The greater the elasticity constant, the stronger the force with which the leaf spring (48) presses the cantilever (14) against the ball bearing (43), and the greater the certain amount of force (51) that is needed to lift the cantilever (14) off the ball bearing (43).

The specific level of the force (51) may be in the range of about 1.5 Newton to about 4.0 Newton, and is preferably held at about 2.0 Newton.

In addition, or as an alternative thereto, it is possible to provide mechanical devices which serve to lift the cantilever (14) of the rocker arm (11) off the outer race (45) of the ball bearing (43). Devices of this type allow for the switching-off of the reciprocating stroke movement (50) of the bristle head (26), and thus of the poking action of the bristles (4), independent of the force (51) at which the user presses the bristles (4) against his dental surfaces. Such a device may for instance be a lever that can be actuated by the user, and which lifts the cantilever (14) off the ball bearing (43). This gives the user the option of activating and deactivating the reciprocating stroke movement of the bristle head (26) at will.

Figure 4:
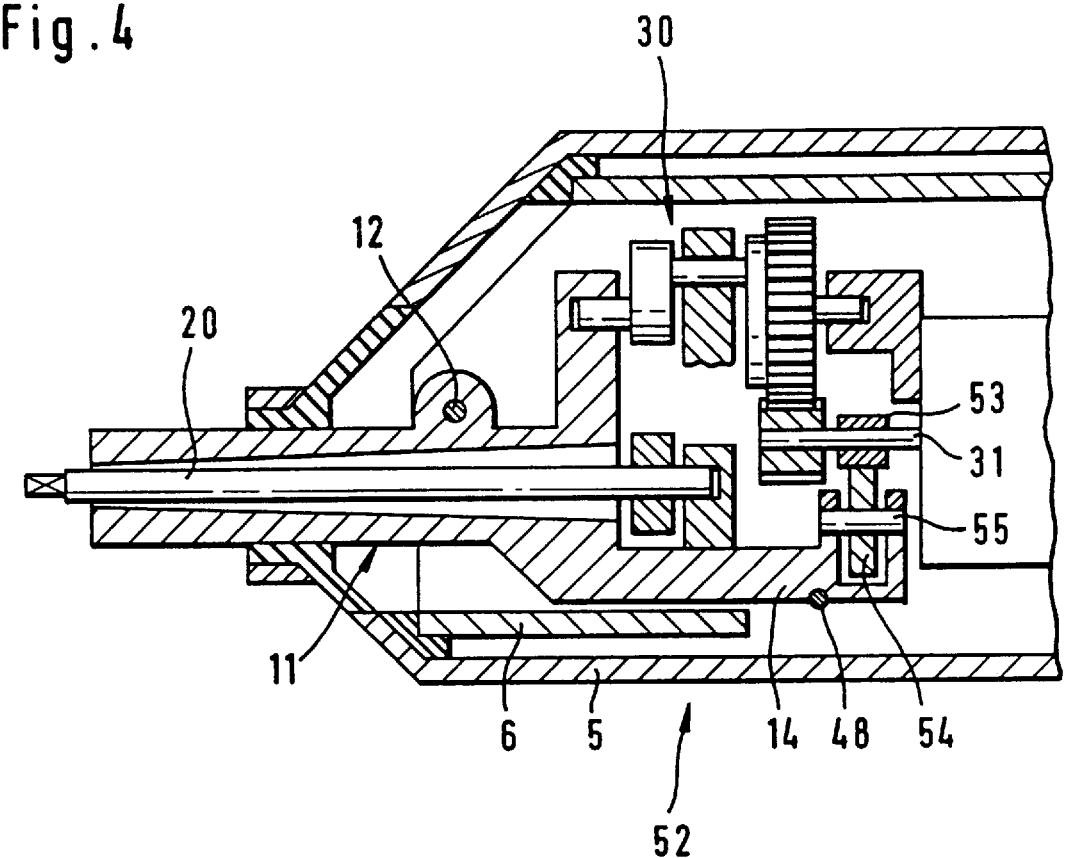
FIG. 4 is a schematic illustration, along a longitudinal section, of a second design example of an electric toothbrush.

FIG. 4 illustrates a second design example of an electric toothbrush (52), which in its configuration and function is very similar to the electric toothbrush (1) per FIGS. 1 to 3. The difference lies in the approach to generating the vibration of the rocker arm (11), which in the electric toothbrush per FIG. 4 is not brought about by a ball bearing with an eccentric inner race. Therefore, the following only describes the components which differ from those in the electric toothbrush per FIGS. 1 to 3. Identical components bear identical reference numbers.

In the electric toothbrush (52) shown in FIG. 4, the vibration is generated by means of an eccentric element (53), which is mounted in fixed position on the motor shaft (31) of the electric motor (8). Said eccentric element may be in the form of a wheel or similar element, which is either seated in off-center fashion, or displays an eccentric circumference. The free end of the cantilever (14) of the rocker arm (11) is provided with a rotating roller (54), which is mounted on a spindle (55) that extends approximately parallel with the motor shaft (31). The roller (54) bears on the eccentric element (53) and, as the motor shaft (31) rotates, it rolls with its circumference along the circumference of the eccentric element (53). As a result, when the electric toothbrush (52) is in the operating mode, the rocker arm (11) is vibrated by the eccentric element (53), and the revolving roller (54) on it. This vibration, as explained above, is transferred to the bristle head (26) where it generates the reciprocating stroke movement (50).

As an alternative to the roller (54), a guide shoe may be provided which slides along the circumference of the eccentric element (53).

Another possible approach involves the use of a ball bearing (43) as shown in FIGS. 1 to 3, with the roller (54) per FIG. 4 being in contact with, and rolling along the circumference of, the outer race (45) of the ball bearing (43).

As another additional or alternative approach, the outer race (45) of the ball bearing (43) is not concentric as shown in FIGS. 1 to 3, but is instead eccentric. When combined with the roller (54), this will generate a vibration which is a composite of the vibration derived from the eccentric inner race (44), and the vibration generated by the eccentric outer race (45).

Another possible alternative is to use an eccentric wheel in lieu of the roller (54), mounted on the cantilever (14) as shown in FIG. 4. To that effect, the wheel is either mounted off-center or it has an eccentric circumference. In this case it is not necessary to equip the wheel with any other component that would be mounted on the motor shaft (31) of the electric motor (8). The eccentric wheel bears directly on the motor shaft (31) and revolves as the motor shaft (31) rotates. Due to the eccentric shape of the wheel, the rocker arm (11) is set in a vibratory motion which, in turn, produces the reciprocating stroke motion (50) of the bristle head (26), and with it the poking action of the bristles (4).

Figure 5:
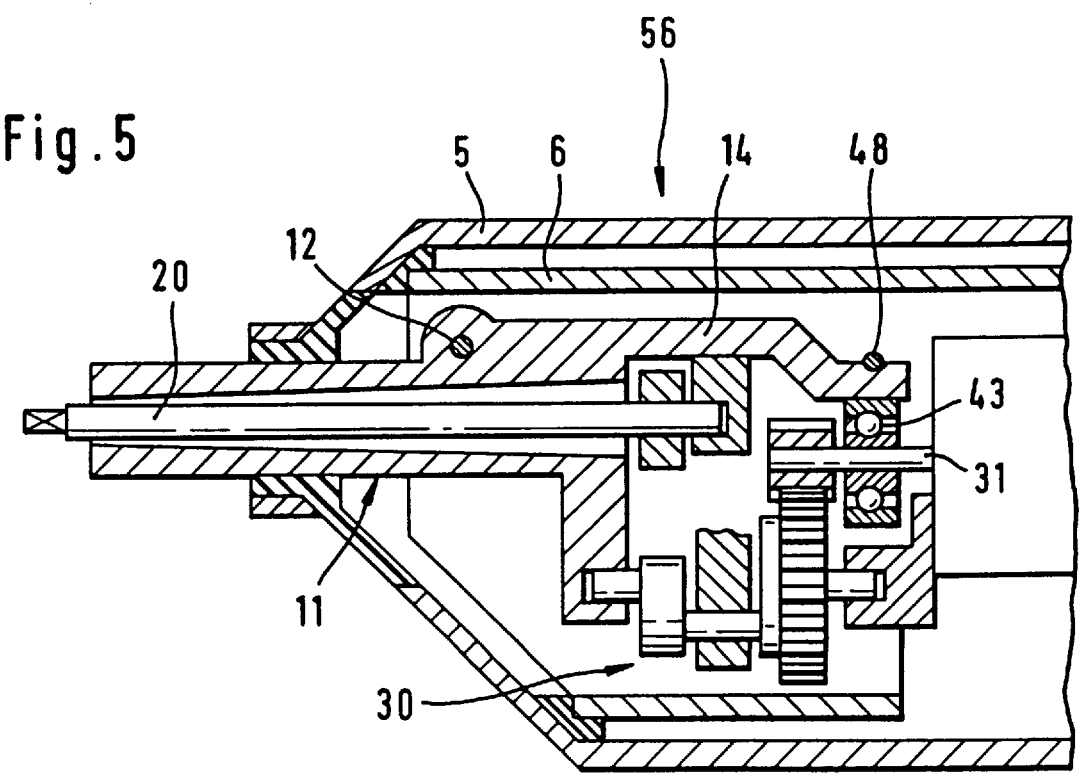
FIG. 5 is a schematic illustration, along a longitudinal section, of a third design example of an electric toothbrush.

FIG. 5 illustrates a third design example of an electric toothbrush (56), which in terms of its structural concept and function is very similar to the electric toothbrush (1), per FIGS. 1 to 3. The only difference is the location of the cantilever (14) of the rocker arm (11), which in the electric toothbrush per FIG. 5 is not on the same side as the bristle head (26). Therefore, the following describes only the components which differ from those in the electric toothbrush (1), per FIGS. 1 to 3. Identical components bear identical reference numbers.

In the electric toothbrush (56), per FIG. 5, the cantilever (14) of the rocker arm (11) bears on the outer race (45) of the ball bearing (43) on that side which is located opposite the bristle head (26). As a result, the cantilever (14) will always be in a state where the leaf spring (48) presses it against the ball bearing (43). Even the force (51) applied on the bristles (4) will not lift the cantilever (14) off the ball bearing (43). In this case, the leaf spring (48) only serves to provide initial spring tension. The reciprocating stroke movement (50) of the bristle head (26), and consequently the poking action of the bristles (4), remain in effect regardless of any force (51).

For space reasons it is necessary in the case of the electric toothbrush (56), per FIG. 5, to position the quadrilateral link (30) on the other side of the rocker arm (11), relative to the electric toothbrush (1), per FIGS. 1 to 3.

Figure 6:
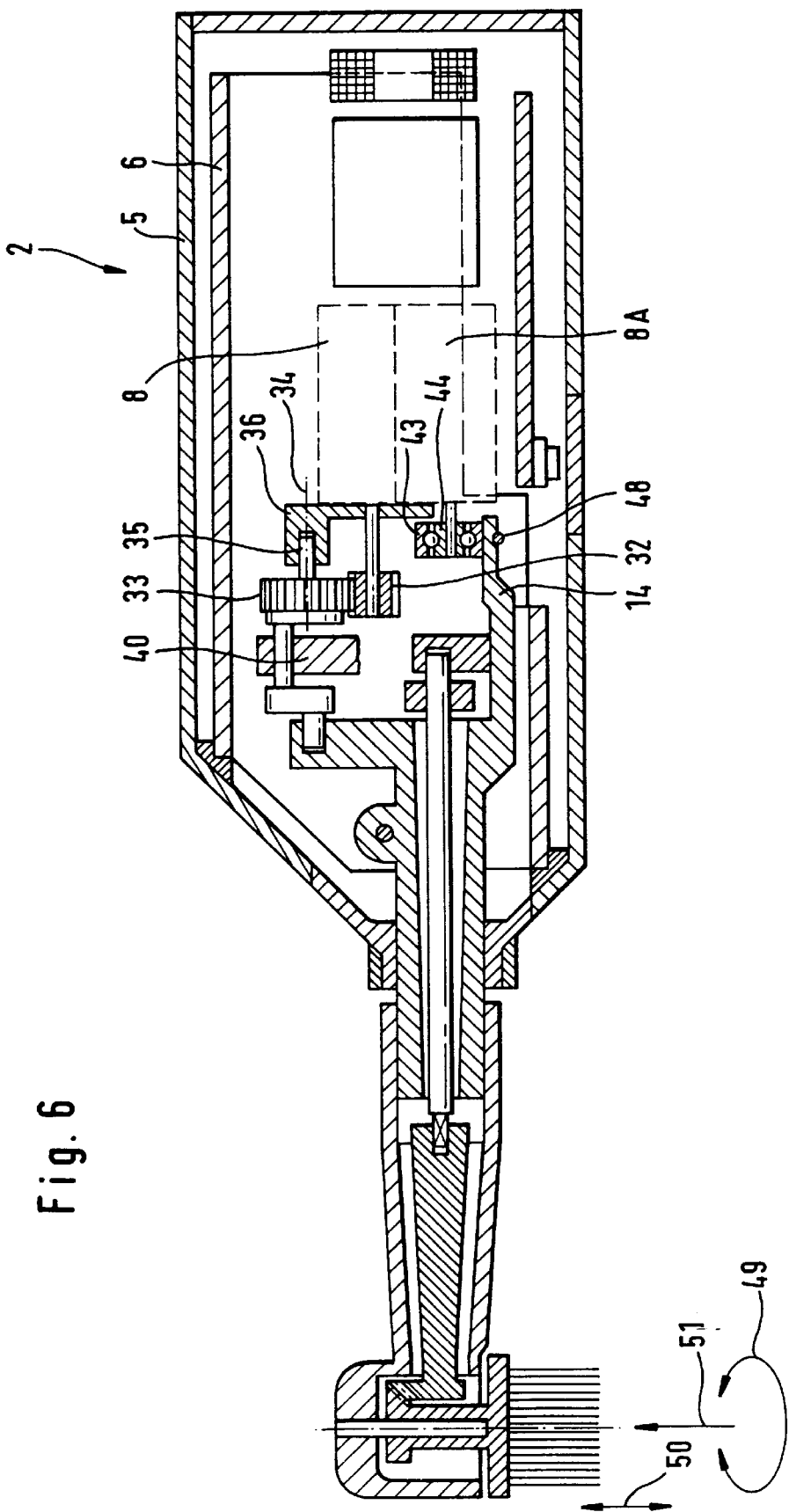
FIG. 6 is a schematic illustration similar to the toothbrush of FIG. 1, showing a variant thereof.

As another possible alternative, the vibration, and with it the reciprocating stroke movement (50) of the bristle head, are not generated by the electric motor (8) as provided for in FIGS. 1 to 5, but by an independent drive system as illustrated in FIG. 6. As a result, the frequency of the reciprocating stroke movement (50) of the bristle head (26), and the frequency of the poking action of the bristles (4), will be independent of the frequency of the alternating rotary movement (49) of the bristle head (26). The separate drive system (8A) for the stroke movement (50) may, for instance, be a second electric motor, or an electromagnetic oscillator, or a piezoelectric actuator.

We claim:

1. An electric toothbrush comprising
   a handle defining a housing in which is disposed an electric motor,
   a shaft displaceably mounted in the housing and extending therefrom along a longitudinal axis, the shaft being operatively connected to the electric motor to be driven in a first direction of motion relative its longitudinal axis and reciprocally driven in a second direction of transverse motion transverse to the shaft longitudinal axis,
   a toothbrush attachment having
      a body member extending along a longitudinal body axis, and
      a bristle head having at least one bristle tuft, the bristle head mounted within the body member for rotary movement relative to the body member about a bristle head pivot axis extending transverse to the longitudinal extent of the body member,
      the body member being adapted to be coupled to the shaft and comprising
   a transmission element directing said shaft motion in the first direction to drive the bristle head about its pivot axis,
   whereby bristles of the bristle head are driven rotatably about the bristle head pivot axis and displaced in a stroke direction generally parallel the bristle head pivot axis.

2. An electric toothbrush as claimed in claim 1, wherein the shaft is supported for said motion in the second direction about a pivot joint disposed in the housing, said pivot joint having an axis (12) extending transverse to the shaft longitudinal axis.

3. An electric toothbrush as claimed in claim 2, wherein the pivot joint comprises a hinge attached to an inner wall of the housing.

4. An electric toothbrush as claimed in claim 1, wherein a frequency of shaft transverse motion in the second direction is greater than a frequency of the bristle head rotary motion.

5. An electric toothbrush as claimed in claim 4, wherein the shaft motion frequency is at least twice the bristle head motion frequency.

6. An electric toothbrush as claimed in claim 1, wherein shaft motion in the transverse direction imparts an amplitude of bristle head displacement in the stroke direction from a rest position of between about ±0.02 mm and about ±0.2 mm.

7. An electric toothbrush as claimed in claim 6, wherein the bristle head stroke amplitude is about ±0.05 mm.

8. An electric toothbrush as claimed in claim 1, wherein a frequency of the bristle head rotary motion is between about 60 to 70 Hz and a frequency of the shaft transverse direction motion is between about 120 to 210 Hz.

9. An electric toothbrush as claimed in claim 8, wherein the bristle head rotary motion frequency is about 65 Hz and the shaft transverse direction motion frequency is about 165 Hz.

10. An electric toothbrush as claimed in claim 1, wherein a ratio of a frequency of the bristle head rotary motion to a frequency of the shaft transverse direction motion is selected so that phase coincidence of heterodyne oscillation does not occur until after a plurality of oscillating cycles.

11. An electric toothbrush as claimed in claim 10, wherein the ratio is selected so that phase coincidence of heterodyne oscillation does not occur until after four oscillating cycles.

12. An electric toothbrush as claimed in claim 1, wherein a ratio of a frequency of the bristle head rotary motion to a frequency of the shaft transverse direction motion is selected from the group of ratios consisting of a finite value, a periodic fraction and a non-periodic fraction.

13. An electric toothbrush as claimed in claim 1, wherein a frequency of the bristle head rotary motion is independent of a frequency of the shaft transverse direction motion.

14. An electric toothbrush as claimed in claim 1, further comprising a second motor disposed in the housing, wherein the second motor drives the shaft in said second direction of transverse motion and said electric motor drives the shaft in said first direction of motion relative its longitudinal axis.

15. An electric toothbrush as claimed in claim 14, wherein the second motor is chosen from the group of motors consisting of an electric motor, an electromagnetic oscillator and a piezoelectric actuator.

16. An electric toothbrush as claimed in claim 1, further comprising a pressure limiting mechanism in the housing acting in response to a force on the bristle head along the second direction transverse to the shaft longitudinal axis exceeding a threshold to stop bristle head motion in the second transverse direction.

17. An electric toothbrush as claimed in claim 1, wherein the brush body transmission element oscillates the bristle head in reciprocating rotary motion about its pivot axis.

18. An electric toothbrush as claimed in claim 1, wherein bristles of the at least one bristle tuft are generally parallel the bristle head pivot axis.

19. An electric toothbrush as claimed in claim 1, further comprising a rocker arm (11) on which the shaft is disposed, the rocker arm being pivotally mounted within the housing about a pivot having an axis extending transverse to the shaft longitudinal axis.

20. An electric toothbrush as claimed in claim 19, wherein
the rocker arm has a cantilever portion extending away from the pivot in a direction opposite a distal end of the shaft that extends away from the housing, and
further comprising a vibration generator disposed in the housing mounted between the electric motor and the cantilever portion, whereby the motor vibrates the rocker arm assembly about the pivot axis.

21. An electric toothbrush as claimed in claim 19, wherein
the rocker arm has a cantilever portion extending away from the pivot in a direction opposite a distal end of the shaft that extends away from the housing, and
further comprising an eccentric element disposed in the housing mounted between a motor shaft of the electric motor and the cantilever portion, whereby the motor vibrates the rocker arm assembly about the pivot axis.

22. An electric toothbrush as claimed in claim 21, wherein the cantilever portion has a guide surface camming against the eccentric element.

23. An electric toothbrush as claimed in claim 22, further comprising a lever mounted on the housing and connected to the rocker arm, the lever being selectively actuated by a user to disengage the cantilever portion from camming against the eccentric element, whereby the second motion in the transverse direction can be shut off.

24. An electric toothbrush as claimed in claim 21, wherein the eccentric element comprises a roller having at least one cam surface against which a guide surface of the cantilever portion bears.

25. An electric toothbrush as claimed in claim 21, wherein the eccentric element comprises a bearing assembly having an eccentric inner race mounted on the motor shaft.

26. An electric toothbrush as claimed in claim 21, wherein the eccentric element comprises an eccentric sleeve having a rotary bearing mounted on the motor shaft.

27. An electric toothbrush as claimed in claim 21, further comprising a spring urging the cantilever portion against the eccentric element.

28. An electric toothbrush as claimed in claim 27, wherein the spring determines a threshold force, whereby in response to a force on the bristle head along the second direction transverse to the shaft longitudinal axis exceeding the threshold force, the cantilever portion is moved out of contacting relation with the eccentric element.

29. An electric toothbrush as claimed in claim 19, wherein the rocker arm comprises a sleeve within which the shaft is disposed.

30. An electric toothbrush as claimed in claim 29, further comprising an elastic diaphragm disposed between the rocker arm sleeve and the housing.

31. An electric toothbrush as claimed in claim 29, wherein the sleeve pivotally mounts the rocker arm to the housing.

32. An electric toothbrush as claimed in claim 19, wherein the shaft and the electric motor are coupled by a four-bar linkage.

33. An electric toothbrush as claimed in claim 19, wherein the rocker arm is supported on a frame disposed within the handle housing.

34. An electric toothbrush as claimed in claim 33, wherein the motor is also disposed on the frame, whereby an inertial mass of the motor is set in motion with the rocker arm.

35. An electric toothbrush as claimed in claim 33, wherein the frame is connected by a resilient mount to the handle housing, thereby tending to isolate vibrations of the rocker arm in operation from a hand of the user.

36. An electric toothbrush as claimed in claim 1, further comprising
a rocker arm (11) on which the shaft is disposed, and
an elastic diaphragm disposed between the rocker arm and the housing, whereby the elastic diaphragm permits the rocker arm to pivot relative the housing about an axis transverse to the shaft longitudinal axis.

37. An electric toothbrush as claimed in claim 1, wherein the bristle head is restrained from displacing axially along its bristle pivot axis relative to the body member.

38. An electric toothbrush as claimed in claim 1, wherein the shaft is mounted in the housing for rotational motion, said shaft first direction of motion being rotational about its longitudinal axis.

39. An electric toothbrush as claimed in claim 38, wherein the shaft first direction rotational motion is oscillatory.

40. An electric toothbrush as claimed in claim 1, wherein the toothbrush attachment is detachably mounted on the shaft.

41. An electric toothbrush as claimed in claim 1, wherein said second direction of transverse motion is perpendicular said shaft longitudinal axis.

42. An electric toothbrush as claimed in claim 1, wherein said bristle head pivot axis extends perpendicular said longitudinal extent of the body member.

43. An electric toothbrush comprising
a handle defining a housing in which is disposed an electric motor,
a shaft assembly displaceably mounted in the housing and extending therefrom along a longitudinal axis, the shaft assembly being operatively connected to the electric motor to be displaced in a transverse direction to the shaft longitudinal axis,
a bristle head mounted for rotary movement on the shaft assembly about a bristle pivot axis extending transverse to the longitudinal extent of the shaft assembly, the bristle head having at least one bristle tuft, and
a transmission linkage disposed in the shaft assembly connected to the electric motor to drive the bristle head about its pivot axis,
whereby bristles of the bristle head move rotatably about the bristle pivot axis and in a direction generally transverse to the shaft assembly longitudinal axis.

44. An electric toothbrush according to claim 43, wherein said transverse direction lies essentially in a single plane containing said longitudinal axis.

45. An electric toothbrush according to claim 43, wherein the bristle head pivot axis and the shaft assembly transverse displacement direction lie in substantially parallel planes.

46. An electric toothbrush according to claim 43, wherein the shaft assembly transmission linkage further comprises a shaft rotatably driven by the motor about its longitudinal axis and connected to the bristle head.

47. An electric toothbrush according to claim 46, wherein the shaft rotational motion is oscillatory.

48. An electric toothbrush handle according to claim 43, wherein a frequency of shaft assembly motion in the transverse direction is greater than a frequency of the bristle head rotary motion.

49. An electric toothbrush according to claim 43, wherein the shaft assembly further comprises an outer sleeve and a shaft disposed within the sleeve, the sleeve being pivotally connected to the housing about an axis transverse to the longitudinal axis.

50. An electric toothbrush according to claim 43, further comprising an eccentric element disposed in the housing connecting a motor shaft of the electric motor to the shaft assembly to vibrate the shaft assembly in the transverse direction.

51. An electric toothbrush according to claim 43, wherein said transverse direction is perpendicular said shaft longitudinal axis.

52. An electric toothbrush as claimed in claim 43, wherein said bristle head pivot axis extends perpendicular said longitudinal extent of the shaft assembly.

53. An electric toothbrush handle comprising a housing in which is disposed an electric motor, a shaft suspended in the housing movably mounted therein and extending therefrom along a longitudinal axis, said shaft being adapted for coupling to a body member of a toothbrush attachment having a bristle head mounted for movement relative to said body member, said shaft being operatively connected to the electric motor to be driven both in a first motion direction relative its said longitudinal axis and reciprocally driven in a second direction transverse to its said longitudinal axis along a transverse movement direction lying essentially in a single plane containing said longitudinal axis, and wherein the shaft is rotatable mounted in the housing, said first direction of motion being rotary motion about the longitudinal axis.

54. An electric toothbrush handle according to claim 53, wherein said rotary motion about the longitudinal axis comprises at least about a 30° arc of travel, said transverse movement having a substantially lesser displacement in said second direction of less than about 0.1 mm.

55. An electric toothbrush handle according to claim 53, wherein the shaft first direction rotational motion is oscillatory.

56. An electric toothbrush handle according to claim 53, wherein said transverse direction is perpendicular said longitudinal axis.

57. An electric toothbrush handle comprising a housing in which is disposed an electric motor, a shaft suspended in the housing movably mounted therein and extending therefrom along a longitudinal axis, said shaft being adapted for coupling to a body member of a toothbrush attachment having a bristle head mounted for movement relative to said body member, said shaft being operatively connected to the electric motor to be driven both in a first motion direction relative its said longitudinal axis and reciprocally driven in a second direction transverse to its said longitudinal axis along a transverse movement direction lying essentially in a single plane containing said longitudinal axis, and wherein the shaft is supported for said motion in the second direction about a pivot joint disposed in the housing, said pivot joint having an axis extending transverse to the shaft longitudinal axis and restraining the shaft against axial displacement parallel its longitudinal axis.

58. An electric toothbrush handle comprising a housing in which is disposed an electric motor, a shaft suspended in the housing movably mounted therein and extending therefrom along a longitudinal axis, said shaft being adapted for coupling to a body member of a toothbrush attachment having a bristle head mounted for movement relative to said body member, said shaft being operatively connected to the electric motor to be driven both in a first motion direction relative its said longitudinal axis and reciprocally driven in a second direction transverse to its said longitudinal axis along a transverse movement direction lying essentially in a single plane containing said longitudinal axis, and wherein a frequency of shaft transverse motion in the second direction is greater than a frequency of the shaft first direction motion.

59. An electric toothbrush handle comprising a housing in which is disposed an electric motor, a shaft suspended in the housing movably mounted therein and extending therefrom along a longitudinal axis, said shaft being adapted for coupling to a body member of a toothbrush attachment having a bristle head mounted for movement relative to said body member, said shaft being operatively connected to the electric motor to be driven both in a first motion direction relative its said longitudinal axis and reciprocally driven in a second direction transverse to its said longitudinal axis along a transverse movement direction lying essentially in a single plane containing said longitudinal axis, and further comprising a rocker arm having a sleeve within which the shaft is disposed, the sleeve being pivotally mounted within the housing about a mounting permitting pivotal motion about an axis extending transverse to the shaft longitudinal axis.

60. An electric toothbrush handle according to claim 59, further comprising an eccentric element disposed in the housing connecting a motor shaft of the electric motor and the rocker arm sleeve, whereby the motor pivotally vibrates the rocker arm assembly about its mounting.

61. An electric toothbrush handle comprising a housing in which is disposed an electric motor, a shaft suspended in the housing movably mounted therein and extending therefrom along a longitudinal axis, said shaft being adapted for coupling to a body member of a toothbrush attachment having a bristle head mounted for movement relative to said body member, said shaft being operatively connected to the electric motor to be driven both in a first motion direction relative its said longitudinal axis and reciprocally driven in a second direction transverse to its said longitudinal axis along a transverse movement direction lying essentially in a single plane containing said longitudinal axis, and further comprising the toothbrush attachment detachably coupled to the shaft, said transverse movement direction being generally parallel to bristles of the bristle head.

62. An electric toothbrush according to claim 61, wherein the toothbrush bristle head rotates on the toothbrush body member.

63. An electric toothbrush handle comprising a housing in which is disposed an electric motor, a shaft assembly suspended in the housing and extending therefrom along a longitudinal axis, said shaft assembly being adapted for coupling to a body member of a toothbrush attachment having a bristle head mounted for movement relative to said body member, said shaft assembly comprising a rocker sleeve and an inner shaft within the sleeve, the rocker sleeve and inner shaft each being driven by the electric motor, said rocker sleeve being restrained from rotary motion about its longitudinal axis and being moveable in a direction transverse to the longitudinal axis, and said inner shaft being displaceably mounted relative to said rocker sleeve.

64. An electric toothbrush handle according to claim 63, wherein the inner shaft is rotatably mounted about its longitudinal axis within the rocker sleeve.

65. An electric toothbrush handle according to claim 64, wherein the inner shaft rotational motion is oscillatory.

66. An electric toothbrush handle according to claim 63, wherein the rocker sleeve is disposed in the housing mounted about a pivot having an axis extending transverse to the shaft assembly longitudinal axis.

67. An electric toothbrush handle according to claim 63, wherein a frequency of rocker sleeve transverse motion is greater than a frequency of the inner shaft motion.

68. An electric toothbrush handle according to claim 63, wherein the inner shaft is concentric with the rocker sleeve.

69. An electric toothbrush handle according to claim 63, further comprising an eccentric element disposed in the housing connecting a motor shaft of the electric motor and the rocker sleeve and vibrating the rocker sleeve in the transverse direction.

70. An electric toothbrush handle according to claim 63, further comprising an elastic diaphragm disposed between the shaft assembly and the housing.

71. An electric toothbrush including the toothbrush handle as claimed in claim 63, and further comprising the toothbrush attachment detachably coupled to the shaft assembly.

72. An electric toothbrush according to claim 71, wherein the toothbrush bristle head rotates on the toothbrush body member.

* * * * *